United States Patent [19]

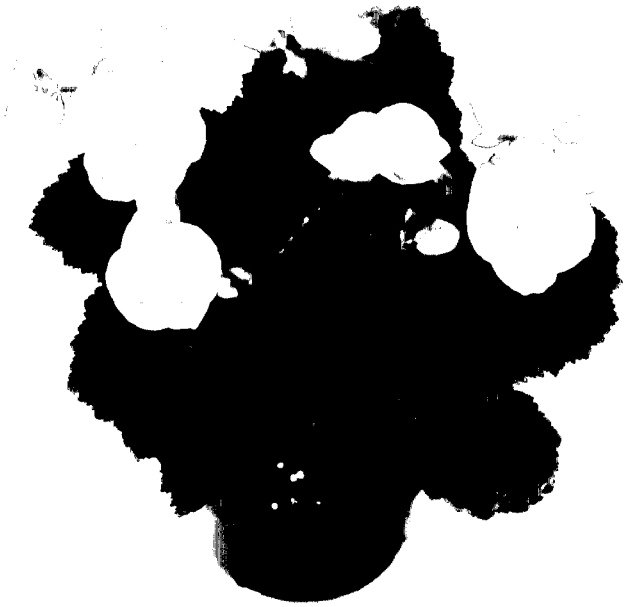

Rohde

[11] Patent Number: Plant 5,747

[45] Date of Patent: May 13, 1986

[54] BEGONIA PLANT NAMED KANON

[75] Inventor: Hans J. Rohde, Nürtingen, Fed. Rep. of Germany

[73] Assignee: Mikkelsens, Inc., Ashtabula, Ohio

[21] Appl. No.: 652,478

[22] Filed: Sep. 20, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A begonia plant named Kanon characterized by its rose pink double sterile flowers up to 6 cm. in diameter, medium size dark green crisp foliage vigorous, upright, self-branching and mounded growth habit, flowering year around, and by its ability to maintain good flower quality for long periods of time.

1 Drawing Figure

The present invention relates to a new and distinctive cultivar of begonia plant, botanically known as *Begonia heimalis, Fotsch* and known by the cultivar name Kanon.

The new cultivar was discovered by me as a mutation of my unpatented cultivar Kascade, and was observed in a group of 14 cm. flowering plants of Kascade growing in a cultivated area.

Asexual reproduction by stem and/or leaf cuttings has reproduced the unique features of the new cultivar through successive propagations.

The following characteristics distinguish Kanon from both its parent and other begonias commercially known and used in the floriculture industry:

1. When compared with Kascade, Kanon is earlier flowering, freer growing; easier to propagate, more floriferous, and has somewhat lighter rose pink flowers with better keeping qualities.

2. In comparison to Aphrodite Pink, disclosed in U.S. Plant. Pat. No. 3,318, Kanon has less tepals (average 18), more vigorous stems tending to be more upright than pendulous, and propagates more readily by leaf cuttings than Aphrodite Pink.

3. In comparison to Elfe, disclosed in U.S. Plant Pat. No. 4,125, and several mutations of Elfe, the flower color is more uniform, the plant more vigorous, propagation slower, and flowering is later for Kanon than Elfe.

4. Improved Schwabenland Pink, disclosed in U.S. Plant Pat. No. 3,628, has single type flowers (4 tepals), large foliage, and more vigorous growth than Kanon.

5. In comparison to Karita, a cultivar of applicant disclosed in an application filed simultaneously herewith, and another mutation of Kascade, the flower color of Kanon is a darker rose pink and flowering is later.

The accompanying colored photograph taken December 1983 illustrates the overall appearance of this cultivar taken as a oblique view of the plant and showing the colors as true as it is reasonably possible to obtain in a colored reproduction of this type.

The following is a detailed description of my new begonia cultivar based on plants produced under commercial practices in glasshouses in Nurtingen, West Germany and Ashtabula, Ohio, and grown in 10 cm. plastic pots. Color references are made to The Royal Horticultural Society Colour Chart except where general color terms of ordinary dictionary significance are used.

Parentage: Mutation of begonia cultivar Kascade.

Propagation:

(A) *Type cutting.*—Leaf cuttings initially under plastic tents.

(B) *Time to root.*—12–15 days at 24° C. summer; 15–20 days at 24° C. winter.

(C) *Rooting habit.*—Fibrous, dendritic, and abundant.

(D) *Time for shoot development.*—for 2 cm. long shoots, 8–9 weeks in summer; 12–13 weeks in winter.

Plant description:

(A) *Form.*—Compact, closely internoded, vigorous, generally self-supporting, herbaceous.

(B) *Habit of growth.*—Upright, self-branching, rapid growth, compact dark green foliage; considered a short to medium height plant.

(C) *Foliage.*—Simple leaves that have vigorous petioles, alternate. (1) Size: 8 cm.×10 cm. on older leaves, diminishing to 4×6 cm. near flowering terminal. Specimen plants in 14 cm. pots may be upwards of 10×14 cm. (2) Shape: generally ovate to orbicular, apice nearly acute, base unequal cordate. (3) Texture: Crisp to firm, top glabrous, underside rugose. (4) Margin: Crenulate. (5) Color: Young foliage top side, nearly yellow green 147A heavily infused with maroon; underside red purple 59A; mature foliage top side, darker than yellow green 147A or 139A, under side near green 148A with tinge of red overtone. (6) Venation: Palmate.

Flowering description:

(A) *Flowering habits.*—Flowering generally occurs in terminal racemes with the inflorescence having 6–8 flowers; once flowering begins, it continues at each succeeding node.

(B) *Natural flowering season.*—Flowering is indeterminant, with flowering occurring in all seasons.

(C) *Flower buds.*—Round to slightly oval, 15–18 mm. in diameter prior to opening, with outer tepals being pink with some green at base.

(D) *Flowers borne.*—On strong self-supporting pedicels originating from vigorous peduncles giving the appearance of a strong plant.

(E) *Quantity.*—Not considered a highly floriferous cultivar, but flowers are uniformly placed to give excellent contrast between foliage and flowers.

(F) *Tepals.*—(1) Shape: Outer tepals nearly round, inner ovate. (2) Color top side in winter when opening, red 52AB, fading to red 52BC, under side red 52B. (3) Number of tepals: Average 20–24, but upwards to 30. (4) Size of tepals: Basal 35 mm. inner to 10 mm. (5) Flower size: Up to 55–60 mm.

(G) *Reproductive organs*: none, cultivar is sterile and presumed to be triploid (4N×2N).

Disease resistance:

No apparent susceptability to powdery mildew or Xanthomonas, the two most common diseases in this type of begonia.

I claim:

1. A begonia plant named Kanon, as described and illustrated, having rose pink double sterile flowers up to 6 cm. in diameter, medium size dark green crisp foliage; vigorous, upright, self-branching and mounded growth habit, flowering year round, and the ability to maintain good flower quality for long periods of time.

* * * * *